(12) United States Patent
Danger (10) Patent No.: US 6,217,330 B1
(45) Date of Patent: Apr. 17, 2001

(54) DENTAL TOOL FOR SURFACE TREATMENT

(76) Inventor: Karl-Heinz Danger, Dreierfeld 8, 32758 Detmold (DE)

( * ) Notice: Subject to any disclaimer, the term of this patent is extended or adjusted under 35 U.S.C. 154(b) by 0 days.

(21) Appl. No.: 09/338,442

(22) Filed: Jun. 22, 1999

Related U.S. Application Data (63) Continuation-in-part of application No. 09/004,470, filed on Jan. 8, 1998.

(30) Foreign Application Priority Data

Oct. 13, 1998 (DE) ................................................ 298 18 265
Nov. 17, 1998 (WO) .................................... PCT/EP98/07379

(51) Int. Cl.[7] ...................................................... A61C 3/06
(52) U.S. Cl. ............................................................. 433/166
(58) Field of Search ..................... 433/166, 165, 433/142; 451/541, 548, 549

(56) References Cited

U.S. PATENT DOCUMENTS

| | | | |
|---|---|---|---|
| 3,858,368 | * 1/1975 | Cocherell et al. | 433/166 |
| 3,982,359 | * 9/1976 | Elbel et al. | 51/295 |
| 5,014,468 | * 5/1991 | Ravipati et al. | 51/295 |
| 5,247,765 | * 9/1993 | Quintana | 51/209.1 |
| 5,273,558 | * 12/1993 | Nelson et al. | 433/166 |
| 5,470,273 | * 11/1995 | Mertens | 451/548 |
| 5,674,122 | * 10/1997 | Krech | 451/536 |

FOREIGN PATENT DOCUMENTS

| | | |
|---|---|---|
| 1 680 659 U1 | 7/1954 | (DE) . |
| 0 623 319 A2 | 7/1989 | (DE) . |
| 0 530 646 A1 | 8/1992 | (DE) . |
| 297 14 199 U1 | 10/1997 | (DE) . |
| 0 898 941 A1 | 7/1998 | (DE) . |
| 197 00 636 C2 | 8/1999 | (DE) . |

* cited by examiner

Primary Examiner—John J. Wilson
(74) Attorney, Agent, or Firm—Sheppard, Mullin, Richter & Hampton LLP (57) ABSTRACT

A dental tool that has a thin disc covered with an abrasive material. The disc has a flange portion and coupling device is formed adjacent to the flange portion for attaching the disc to a drive device. The drive device spins the disc to treat a dental surface. The thickness of the disc may decrease from a central portion of the disc toward a peripheral edge of the disc. The disc may be interspersed with an abrasive material integrated into the disc by an elastic bond.

25 Claims, 6 Drawing Sheets

DENTAL TOOL FOR SURFACE TREATMENT

The present invention relates to a dental tool for surface treatment, and in particular for polishing or grinding teeth or dentures. This is a continuation-in-part of application Ser. No. 09/004,470, filed Jan. 8, 1998, which is incorporated herein by reference. Priority also is claimed based upon German Application No. 29818265.3, filed Oct. 13, 1998, and PCT application No. PCT/EP98/07379, filed Nov. 17, 1998.

BACKGROUND OF THE INVENTION

In the dental field, for instance when teeth or dentures are prepared, many tasks require the use of dental tools that grind, polish or otherwise treat a desired surface. Some dental tools have grinding heads coated with aluminum oxide and are known in the art. However, such dental tools have heads that are too thick to be used on small interdental spaces and in the treatment and shaping of some fillings. Such grinding heads are also not flexible enough to allow a dentist to easily treat rounded surfaces in interdental spaces.

Furthermore, known dental tools for surface treatment have a drawback that they wear relatively rapidly and thus have only a short service life. Moreover, because they wear out rapidly, the head of such a tool must often be changed during the treatment of a particular dental surface, such as a tooth or a denture.

Accordingly, there is a need for an improved dental tool for surface treatment that is flexible, has a longer service life, and is thin so as to provide for treatment of rounded surfaces in interdental spaces. The present invention satisfies need.

SUMMARY OF THE INVENTION

The present invention provides an improved dental tool for surface treatment that is easy to make, reliable, flexible, thin, and has a long service life. The tool is flexible and this so as to provide for treatment of surfaces in interdental spaces.

In particular, the dental tool of the invention is intended for attachment to a dental drive device and to be used for polishing or grinding a surface. The dental tool includes a thin disc covered with an abrasive material and having a central portion and a peripheral edge. A flange is located on the central portion of the disc and a coupling device is located adjacent to the flange. The coupling device is configured to attach to the drive device.

In one embodiment of the invention, the thickness of the disc decreases from its central portion toward its peripheral edge. In another embodiment, the disc is interspersed with the abrasive material and the abrasive material is integrated into the disc by an elastic bond. This embodiment need not include the flange. Such an elastic bond preferably is provided by the use of a silicon material.

A disc constructed with the decreasing thickness described above has excellent stability because it is thicker in its central portion than on its edge portion. Conversely, the reduced thickness towards the disc's outer circumference improves the flexibility of the tool. The edge portion of the disc can be made very thin so that narrow interdental spaces can advantageously be treated.

In a detail of the invention, the flange may be integrally formed into the disc. As a result, the dental tool can be easy to produce because the disc and the flange can be made from one material. Hence, the dental tool can advantageously be made, for example, entirely from polishing or grinding material, i.e. from a carrier or binding material interspersed with abrasive material. The production of the dental tool can thereby be simplified considerably. Furthermore, a structure may thereby be achieved wherein the dental tool is covered with abrasive material on its upper and lower sides and is very thin. The disc can thus be used, for example, on interdental spaces in such a manner that it is advantageously operative on both sides.

In one detail of the invention, the thickness of the disc may continuously decrease from its central portion towards its edge portion. It is thereby possible to achieve predetermined geometric configurations on the disc of the dental tool, which considerably simplifies use of the tool. For example, the upper side of the disc may be located in one plane and the bottom side of the disc may approach the upper side toward the peripheral edge of the disc. Alternatively, the bottom side may have a parabolic or other configuration when viewed in cross section, as is required by different applications.

With regard to the embodiment of the invention that includes a disc interspersed with abrasive material, the disc is made of a carrier material with abrasive material disposed therein. As a result, both the upper side and the bottom side of the disc may be provided with abrasive material so that both surfaces can advantageously be used for dental surface treatment. The abrasive material is integrated into the disc through an elastic bond.

Preferably, the dental tool may have a regular surface structure consisting of projecting portions and recessed portions. The projecting portions provide an abrasive effect and recessed portions have little or no abrasive effect. A high degree of flexibility is achieved, in particular, because of the thin configuration of the disc used in combination with the elastic bond of the abrasive material. Since it is not the whole surface of the disc that has an abrasive effect, heat buildup is reduced during use if the inventive dental tool. Furthermore, the projecting portions are unlikely to clog with surface chips because the recessed portions serve as chip receiving chambers.

The inventive dental tool can be used for treating strongly curved surfaces without the disc being deformed in a permanent manner, and hardly accessible places, e.g. interdental spaces, can be treated in an adequate manner. Furthermore, very good grinding or polishing results can be achieved due to the structure of the surface of the disc, with a glossy shine of the tooth surface being achievable during polishing.

According to the invention, the surface structure of the disc may be regular or irregular. Hence, depending on the application, various patterns of disc surfaces can be produced. A regular surface structure can, for example, be provided by simply forming the projecting portions or the recessed portions in geometric or other defined forms. The projecting portions may, for example, define honeycombed, circular, hexagonal or octagonal shapes. The projecting portions formed in this manner may be interconnected, for instance, by means of webs. Any desired combination of the above-mentioned forms are possible.

In an advantageous development of the invention, the projecting portions and the recessed portions are designed either as embossments or as continuous openings or penetrations through the disc. The continuous openings are of particular advantage because they permit an improved heat dissipation and chip discharge from the disc. Furthermore, the penetrations can be used for the supply of a coolant. By comparison, dental tools which comprise intermediate portions formed as an embossments have an improved strength in comparison with penetrations.

It should be appreciated that the openings or penetrations make it possible for the user to view the surface to be treated during treatment. In particular, as the disc spins, the surface to be treated can be observed through the rapidly-spinning openings. Hence, a dentist can monitor the polishing or grinding operation during treatment without having to remove the dental tool from this surface.

A coupling device is provided for connecting the dental tool to a drive device. The coupling device may be configured as a centrical hole or as a quick-change coupling means. The quick-change coupling device primarily is a blind hole provided on the flange portion of the disc. Hence, the dental tool can be clamped onto disc carriers that are commonly used in dental offices.

When the quick-change coupling means is used, the dental tool according to the invention can be coupled onto the drive means within a short period of time without any troublesome clamping action. Since no strength-reducing central opening is provided on a disc made in such a configuration, the strength of the disc is improved and the above abrasive surface structure can be provided over the entire surface of the disc.

To further reduce heat buildup during the use of the dental tool, abrasive material of different grain sizes may be provided on the projecting portions. For instance, portions of different grain sizes may be arranged alternately. Furthermore, it can be of advantage to provide a combination of continuous openings and recesses. For instance, the strength of the disc can be enhanced if embossments are only located in the central portion of the disc whereas continuous openings are located on the edge of the disc. As a result, the edge of the disc will be more flexible.

Other features and advantages of the invention will become apparent from the following detailed description taken in conjunction with the accompanying drawings, which illustrate, by way of example, the principles of the invention.

DETAILED DESCRIPTION OF THE PREFERRED EMBODIMENT

Figure 1:
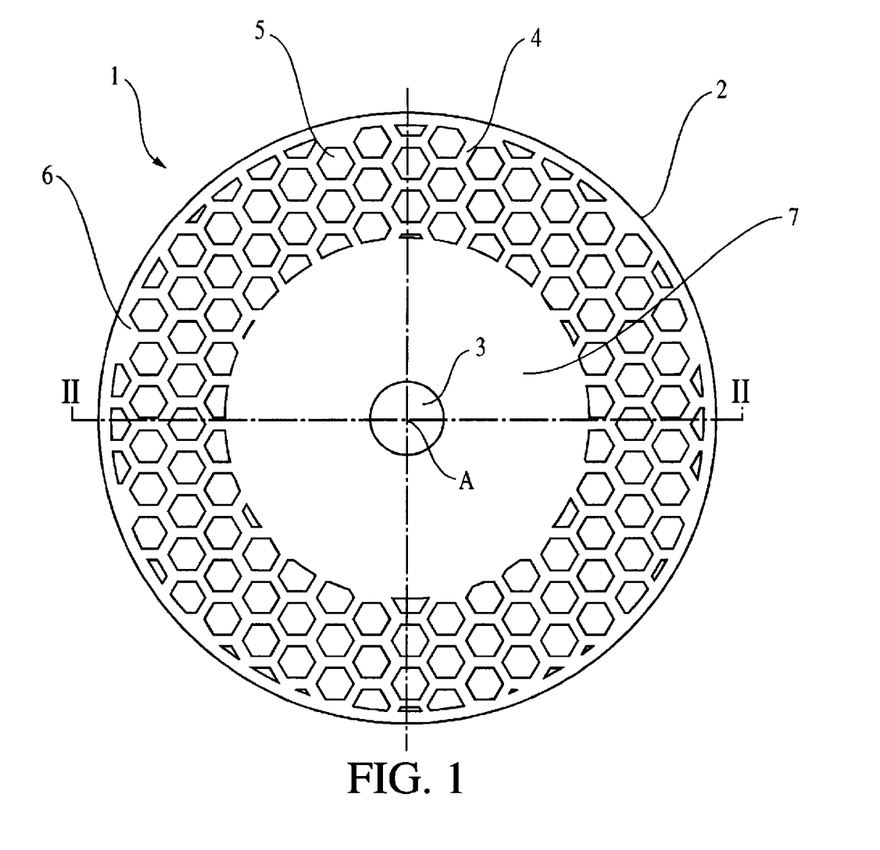
FIG. 1 is a top plan view of a first embodiment of a dental tool according to the present invention.
Figure 2:
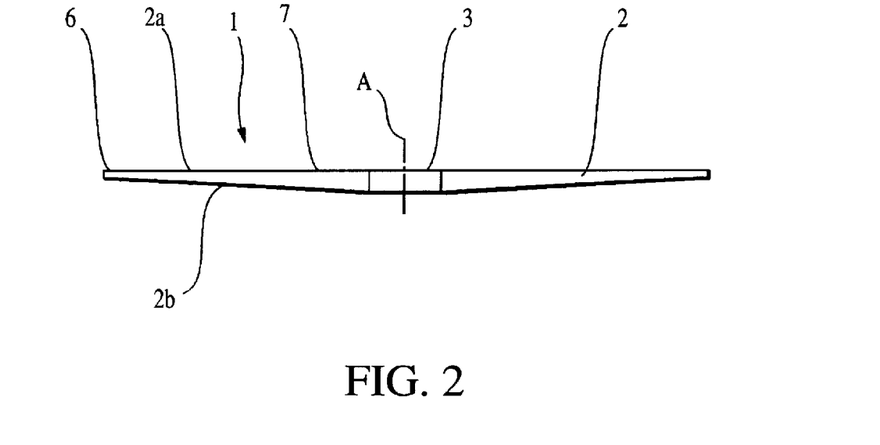
FIG. 2 is a schematic sectional view along line II—II of FIG. 1.

FIGS. 1 and 2 show a first embodiment of an inventive dental tool 1 for surface treatment, and in particular for grinding or polishing of a dental surface. The dental tool 1 includes a thin flat disc 2 which is covered with an abrasive material and which includes projecting portions 4 and recessed portions 5. As shown in FIG. 1, the projecting portions 4 are web-shaped and are adjacent to the edge portion 6 of the disc 2. The webs define the recessed portions 5 which do not contact the tooth surface during use of the dental tool. The recessed portions preferably may be honeycomb-shaped recesses and serve, in particular to receive tooth chips, or the like.

The dental tool 1 of the first embodiment is made as one piece and has a carrier material interspersed with an abrasive material. Abrasive material that projects outwardly is also provided on the outer surfaces of the dental tool.

On a center portion 7 of the disc 2 the projecting portion 4 does not have any recessed portions. The center portion 7 of the disc 2 is covered with abrasive material which during polishing or grinding comes into contact with the tooth or denture to be treated. However, it is also possible to configure the center portion 7 in a recessed fashion so that abrasive material is less likely to make contact during polishing or grinding.

As shown in FIGS. 1 and 2, the disc 2 has a central opening 3 with a central axis A. The central opening 3 can be attached by a common coupling device (not shown) to a common drive device (not shown), as is known in the art. In particular, the dental tool 1 can be attached via its opening 3 into a free end of a drive shaft that is, in turn, connected to a drive device that spins the tool 1. As is apparent from FIG. 2, a flange portion which has formed thereon the central opening 3 is directly integrated into the disc 2.

As shown in FIG. 2, the thickness of the disc 2 tapers from the central portion 7 towards the edge portion 6. In this embodiment, the thickness is reduced in linear fashion. However, parabolic or stepped thickness variations are also possible. As shown in FIG. 2, the disc 2 has an upper side 2a and a bottom side 2b. The upper side 2a is positioned in a plane which the bottom side 2b extends to in inclined fashion, so that the thickness of the disc 2 decreases from the center to the edge portion 6. Both the upper side 2a and the bottom side 2b of the disc 2 preferably comprise abrasive material so that the dental tool 1 has two working surfaces.

Figure 3:
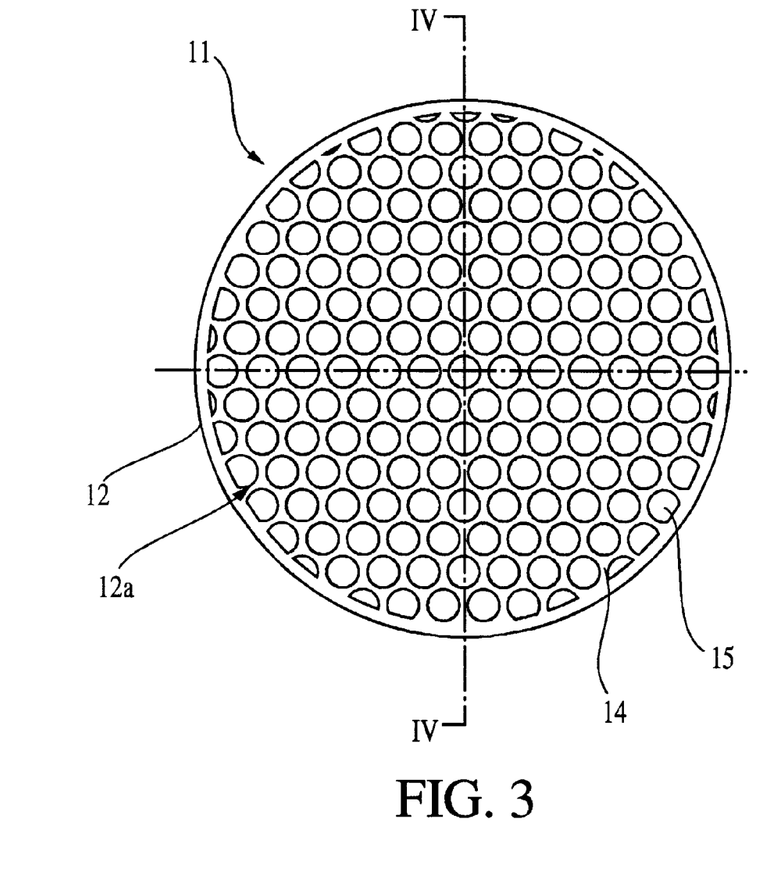
FIG. 3 is a top plan view of a second embodiment of a dental tool according to the present invention.
Figure 4:
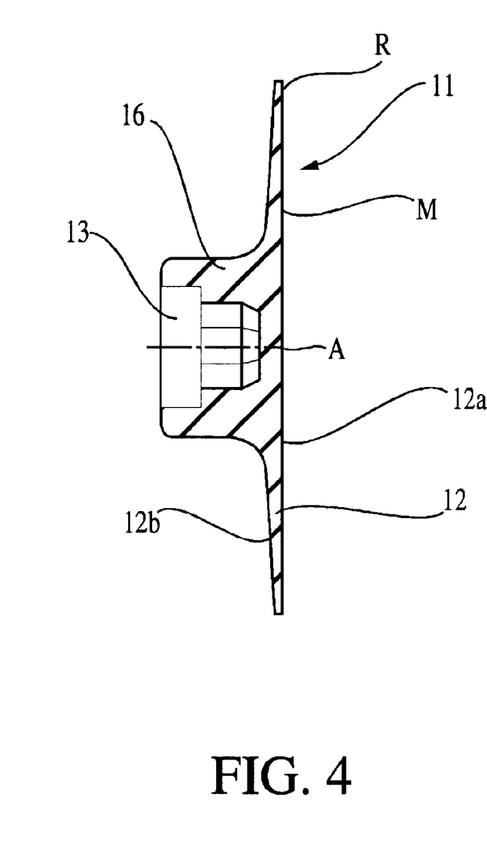
FIG. 4 is a schematic cross-sectional view along line VI—VI of FIG. 3.

FIGS. 3 and 4 show a second embodiment of a dental tool 11. The dental tool 11 the second embodiment comprises a disc 12, a flange portion 16 and a coupling device 13. As shown in FIG. 4, the coupling device 13 consists of a blind hole which serves to receive a shaft of a drive device (not shown) which can be of any type commonly available in the dental art. The drive device has a common locking mechanism (not shown) to engage the dental tool 11 via the blind hole 13.

As shown in FIG. 4, the thickness of the disc 12 increases from the edge R toward a central portion M which has the flange 16 disposed thereon. As a result, the stability and rigidity of the dental tool increases from the outside edge toward the center, with a high flexibility being maintained on the edge portion R thanks to the relatively small thickness in that area of preferably about 0.2 to 0.3 mm.

In the second embodiment, the flange 16 and the disc 12 are integrally made from a carrier material interspersed with abrasive material. Advantageously, the carrier material serves as an elastic bond, i.e. the carrier material is elastic to a certain degree. This permits an easy manufacture of the dental tool according to the invention. Since this embodiment a continuous opening does not exist around the central axis A for receiving a shaft of a drive device, a high stability is obtained.

As shown in FIG. 3, the dental tool 11 of the second embodiment has an upper side 12a with circular recessed portions 15 that are each defined by projecting portions 14 formed as webs. In this embodiment, such surface structure is provided on the whole upper side 12a of the disc 12.

FIGS. 5–11 show further embodiments of inventive dental tools 11 which have similar structure as the second embodiment shown in FIGS. 3–4. Differences between the individual embodiments are primarily due to the webs and recesses comprising the surface structure of the upper sides 12a of the discs 12 in these figures.

Figure 5:
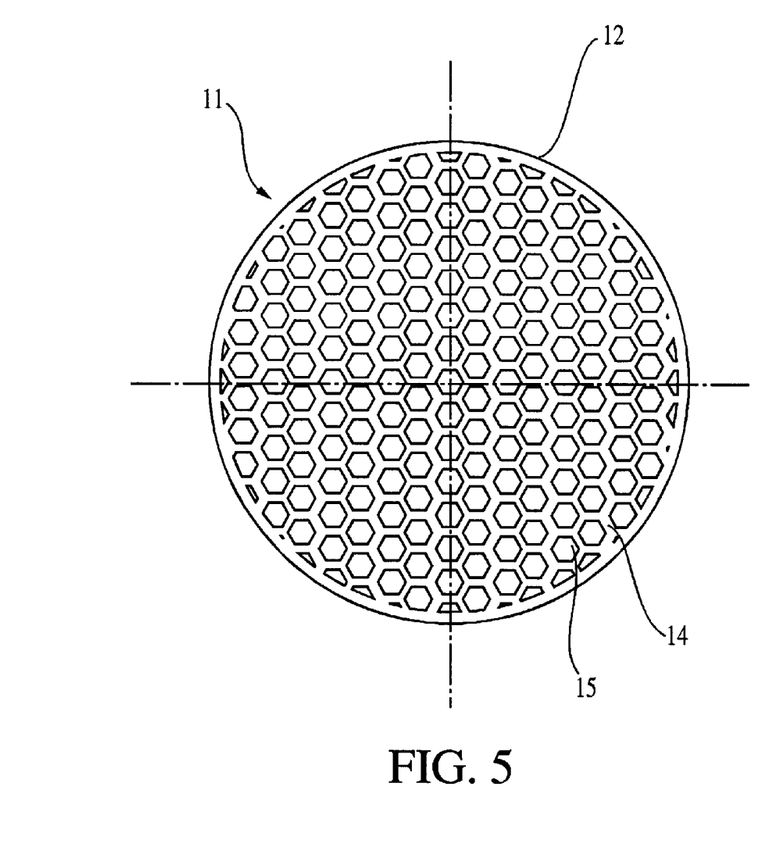
FIG. 5 is a top plan view of a third embodiment of a dental tool according to the present invention.
Figure 6:
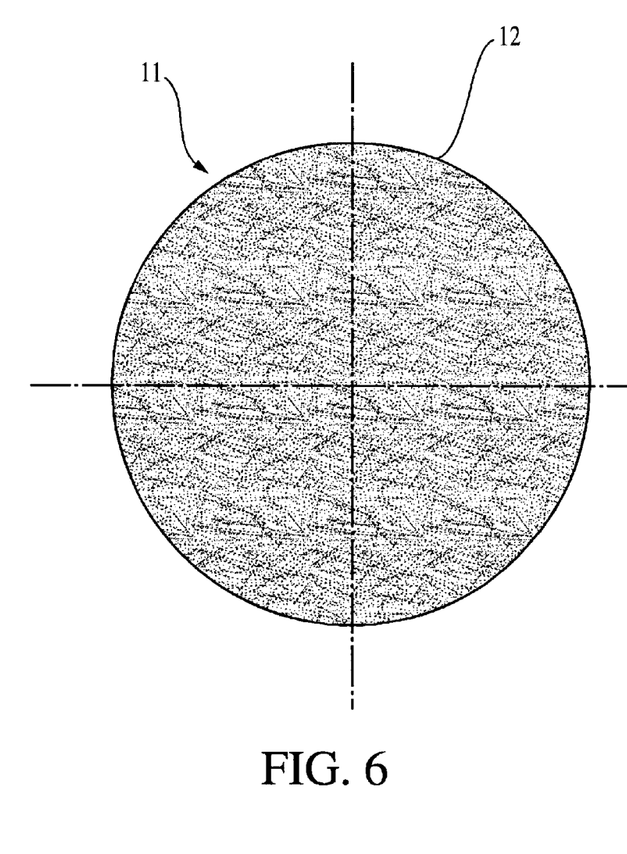
FIG. 6 is a top plan view of a fourth embodiment of a dental tool according to the present invention.
Figure 7:
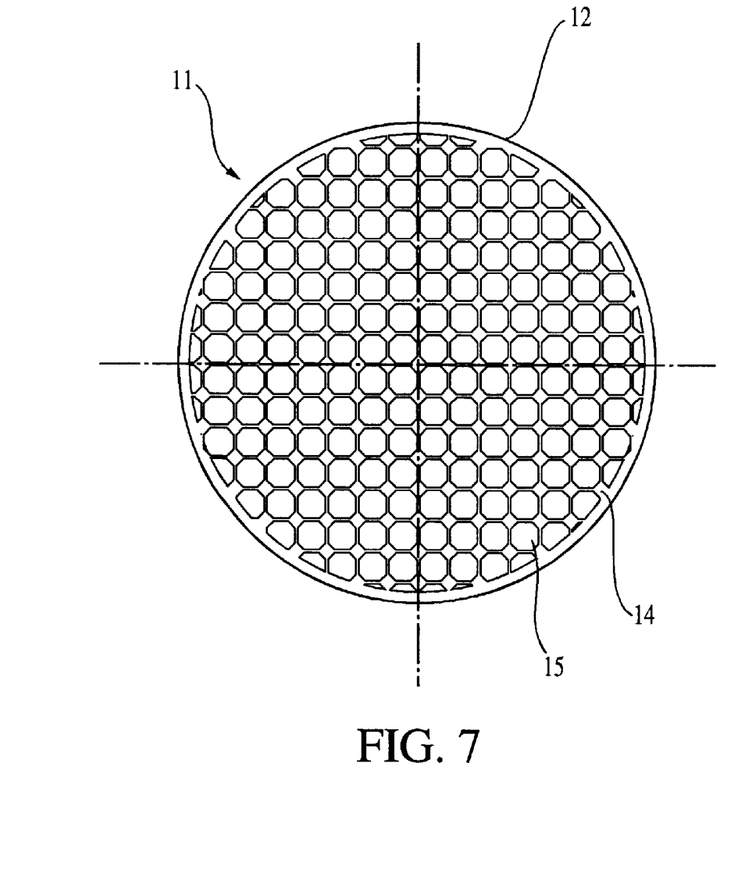
FIG. 7 is a top plan view of a fifth embodiment of a dental tool according to the present invention.
Figure 8:
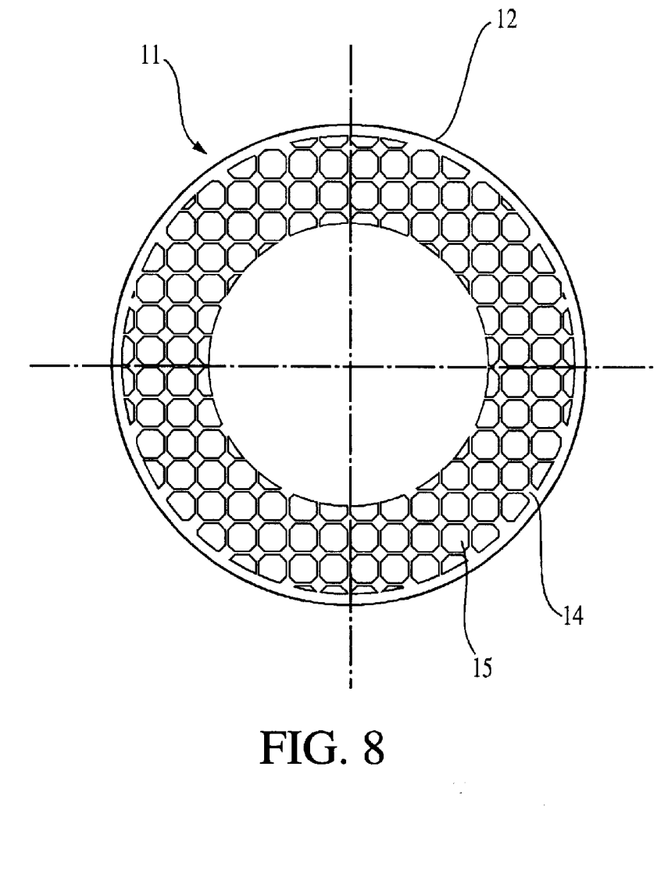
FIG. 8 is a top plan view of a sixth embodiment of a dental tool according to the present invention.
Figure 9:
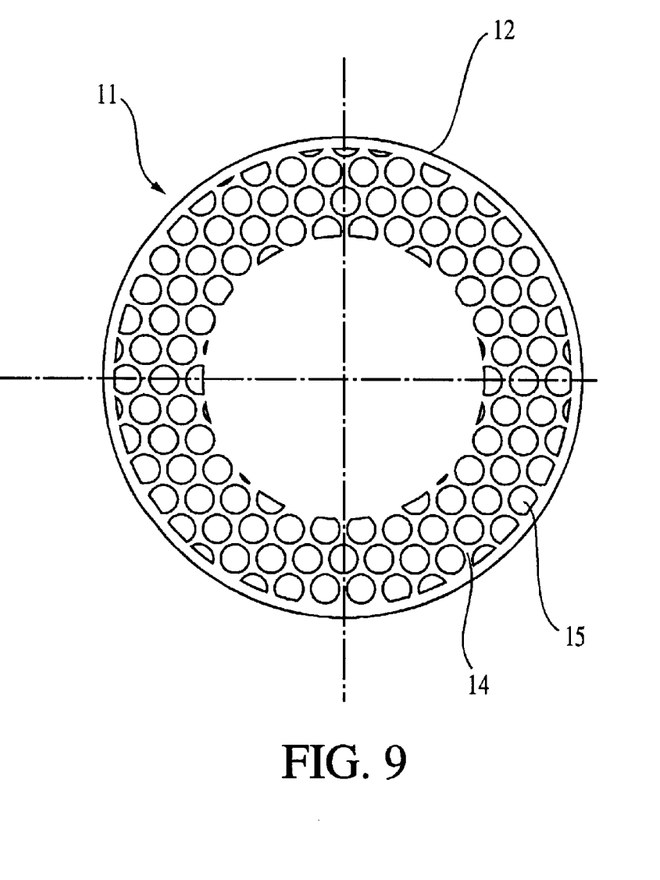
FIG. 9 is a top plan view of a seventh embodiment of a dental tool according to the present invention.
Figure 10:
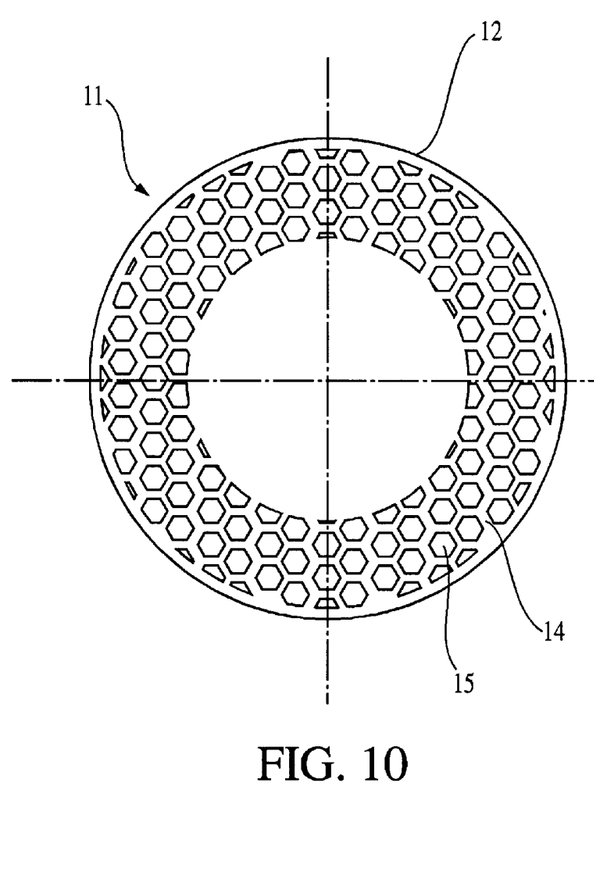
FIG. 10 is a top plan view of an eighth embodiment of a dental tool according to the present invention.
Figure 11:
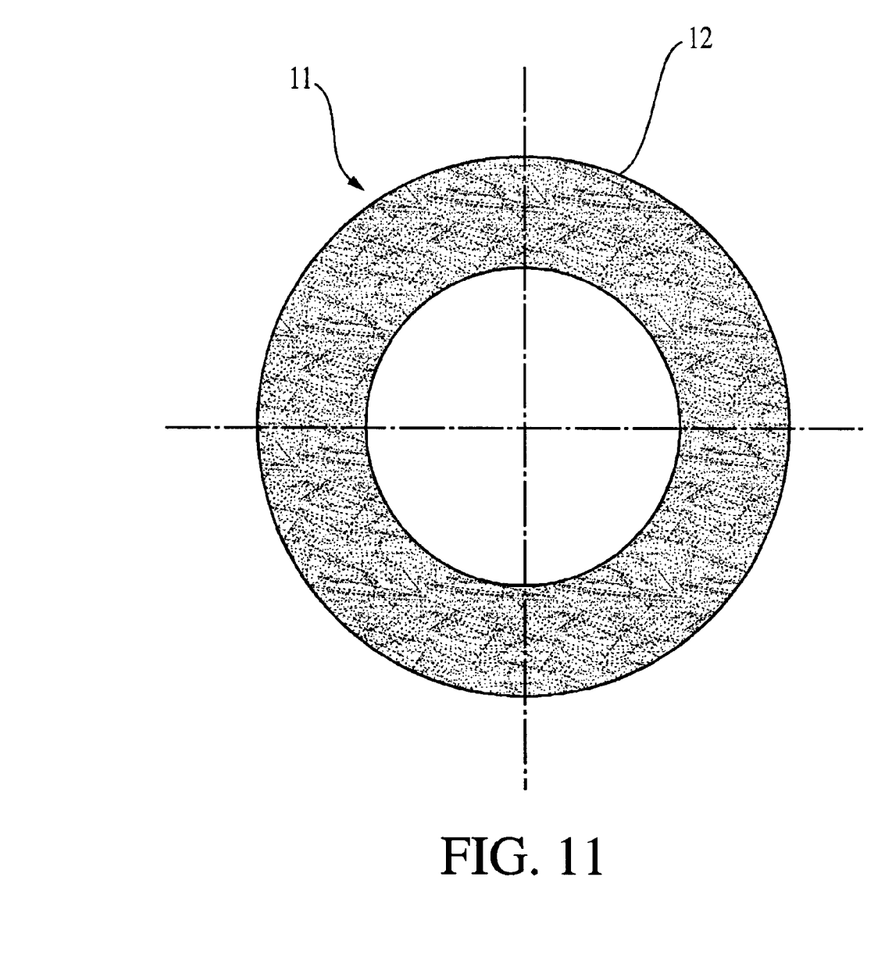
FIG. 11 is a top plan view of a ninth embodiment of a dental tool according to the present invention.

FIGS. 5–7 show embodiments that have a regular surface structure over the entire surface of the disc 12. The embodiment shown in FIG. 5 has honeycomb-shaped recessed portions 15, each defined by web-like projecting portions 14. The embodiment illustrated in FIG. 6 has an irregular surface structure which can for example easily be accomplished by using abrasive material of different grain sizes. Hence, the spaces formed between the individual grains of the abrasive material are the recessed portions. FIG. 7 shows an embodiment with a regularly formed surface structure that is formed by octagonal recessed portions 15 with intermediately arranged projecting webs 14.

FIGS. 8 to 11 illustrate dental tools 11 having the regular and irregular surface structures of the upper sides 12a of the discs 12 shown in the preceding embodiments, except that the surface structure is arranged on a relatively broad edge portion of each disc 12. The inner circular portion can either be configured as a recessed portion or as a projecting portion, depending on the requirements of a particular application.

It should be noted with respect to all of the above-described embodiments that the recesses 15 can be configured as openings 15 extending through the disc 12. Such openings allow the user to view the surface to be treated as the tool is spinning during treatment. In addition, in order to achieve different flexibilities of the dental tool 11, it can be configured with any desired combination of recesses, webs, or openings. To achieve a flexibility that is as high as possible, penetrations or openings can be located on the edge portions of the disc 12. Depending on the particular application, the recessed portions of a disc 12 may be provided only on part or on the entire upper side and/or bottom side of the disc. Moreover, the upper side and bottom side of the disc 12 may have different surface structures.

Preferably, the disc 12 has a thickness of 0.2 to 0.3 mm its edge 7. Thus, portions in interdental spaces (such as small spaces between teeth) can, in particular, be treated in an easy manner and with adequate accuracy. In addition, the disc has a sufficient stability because of the thicker central portion 7 of the disc. The disc preferably has a diameter between 8 mm and 22 mm. However, it is also possible to use larger discs of up to 30 mm, in particular for making veneer crowns or bridges.

All of the illustrated embodiments may include a coupling device configured either as a centrally drilled hole with a central axis A or a blind hole suited for a common quick-change coupling means. Preferably, the hole diameter is about 1.6 to 2.3 mm. The webs also can be configured as the recessed portions and the interposed portions for example, the circular or honeycomb-shaped portions, can be configured as the projecting portions. Moreover, the different shapes of the recessed and projecting portions may be combined in any desired manner, as required for a particular application.

To achieve a high elasticity of the disc 12, the elastic bond of the abrasive material may be made of silicon. If silicon is used, the connection between the abrasive material and the carrier material should be very elastic. Thus, the flexibility of the inventive disc 12 can be improved considerably by means of the elastic bond. Other suitable elastic materials may however also be used as the elastic bond. Aluminum oxide, silicon carbide or diamond materials may be used as the abrasive material.

While particular forms of the invention have been illustrated and described, it will be apparent that various modifications can be made without departing from the spirit and scope of the invention. Thus, although the invention has been described in detail with reference only to the preferred embodiments, those having ordinary skill in the art will appreciate that various modifications can be made without departing from the invention. Accordingly, the invention is not intended to be limited, and is defined with reference to the following claims.

I claim:

1. A dental tool for surface treatment for attachment to a dental drive device, the tool comprising:
   a thin disc covered with an abrasive material and having a central portion and a peripheral edge;
   a flange located on and integrally formed onto the central portion of the disc; and
   a coupling device adjacent to the flange, the coupling device configured to attach to the drive device;
   wherein the thickness of the disc decreases from its central portion toward its peripheral edge; and
   wherein the disc and the flange portion are interspersed with abrasive material.

2. The dental tool of claim 1, wherein the thickness of the disc decreases continuously from the central portion to the edge of the disc.

3. The dental tool of claim 1, wherein the disc further comprises an upper side and a bottom side, the upper side being arranged in a predetermined plane and the bottom side being configured to approach the upper side toward the edge of the disc.

4. A dental tool for surface treatment for attachment to a dental drive device, the tool comprising:
   a thin disc having a first surface covered with abrasive material; and
   a coupling device on the disk, the coupling device configured to attach to the drive device;
   wherein the disc is interspersed with the abrasive material, the abrasive material being integrated into the disc by an elastic bond; and
   wherein the first surface of the disc comprises projecting portions and recessed portions arranged in a predetermined pattern.

5. The dental tool of claim 4, wherein the recessed portions are openings extending through the disc.

6. The dental tool of claim 4, wherein the recessed portions are hexagonal.

7. The dental tool of claim 6, wherein the recessed portions and the projecting portions cooperatively define a honeycomb-shaped area on the first surface of the disc.

8. The dental tool of claim 6, wherein the recessed portions are circular.

9. The dental tool of claim 4, wherein the recessed portions are octagonal.

10. The dental tool of claim 4, wherein the projecting portions are configured as webs defining the recessed portions.

11. The dental tool of claim 4, wherein the first surface of the disk comprises an irregular surface structure having projecting portions and recessed portions.

12. The dental tool of claim 11, wherein the recessed portions are openings extending through the disc.

13. The dental tool of claim 4, wherein the coupling device is a central hole.

14. The dental tool of claim 4, wherein the coupling device is a quick-change coupling.

15. The dental tool of claim 4, wherein the projecting portions comprise sections with different abrasive materials.

16. The dental tool of claim 4, wherein the projecting portions comprise sections with different abrasive grain sizes.

17. The dental tool of claim 4, characterized in that the elastic bond is made by a silicon material.

18. The dental tool of claim 4, wherein the thin disk is a unitary structure, and wherein the recessed portions are holes defined in the unitary structure.

19. A dental tool for surface treatment for attachment to a dental drive device, the tool comprising:

a thin disc having a first surface and a peripheral edge, the first surface covered with abrasive material and defining projecting portions and recessed portions arranged in a predetermined pattern;

a coupling device on the disk, the coupling device configured to attach to the drive device;

wherein the disc is interspersed with the abrasive material, the abrasive material being integrated into the disc by an elastic bond made by a silicon material; the projecting portions and the recessed portions being located in a predetermined area extending radially inwardly from the peripheral edge of the disc a predetermined distance.

20. The dental tool of claim 19, wherein the recessed portions are openings extending through the disc.

21. The dental tool of claim 19, wherein the recessed portions are hexagonal.

22. The dental tool of claim 21, wherein the recessed portions and the projecting portions cooperatively define a honeycomb-shaped area on the first surface of the disc.

23. The dental tool of claim 19, wherein the recessed portions are circular.

24. The dental tool of claim 19, wherein the recessed portions are octagonal.

25. The dental tool of claim 19, wherein the projecting portions are configured as webs defining the recessed portions.

* * * * *